United States Patent [19]

Livingston et al.

[11] Patent Number: 4,565,889

[45] Date of Patent: Jan. 21, 1986

[54] PROCESS FOR THE PRODUCTION OF N-(3-DIMETHYLAMINOPROPYL)METHACRYLAMIDE

[75] Inventors: David R. Livingston; Edward E. McEntire; Edward C. Nieh, all of Austin, Tex.

[73] Assignee: Texaco Inc., White Plains, N.Y.

[21] Appl. No.: 588,826

[22] Filed: Mar. 12, 1984

[51] Int. Cl.$^4$ ............................................. C07C 102/00
[52] U.S. Cl. ..................................................... 564/205
[58] Field of Search ........................................... 564/205

[56] References Cited

U.S. PATENT DOCUMENTS

| | | | |
|---|---|---|---|
| 3,354,208 | 11/1967 | Welcher | 564/205 |
| 3,878,247 | 4/1975 | Moss et al. | 260/561 |
| 4,251,461 | 2/1981 | Livingston | 564/204 |
| 4,287,363 | 9/1981 | McEntire | 564/205 |

Primary Examiner—Paul F. Shaver
Attorney, Agent, or Firm—Jack H. Park; Kenneth R. Priem

[57] ABSTRACT

N-(3-dimethylaminopropyl)methacrylamide is prepared by the non-catalytic pyrolysis of N-(3-dimethylaminopropyl)-3-dimethylaminopropyl-2-methyl propionamide in a closed reactor. The N-(3-dimethylaminopropyl)methacrylamide is not removed from the reaction mixture until the pyrolysis reaction is completed.

4 Claims, 1 Drawing Figure

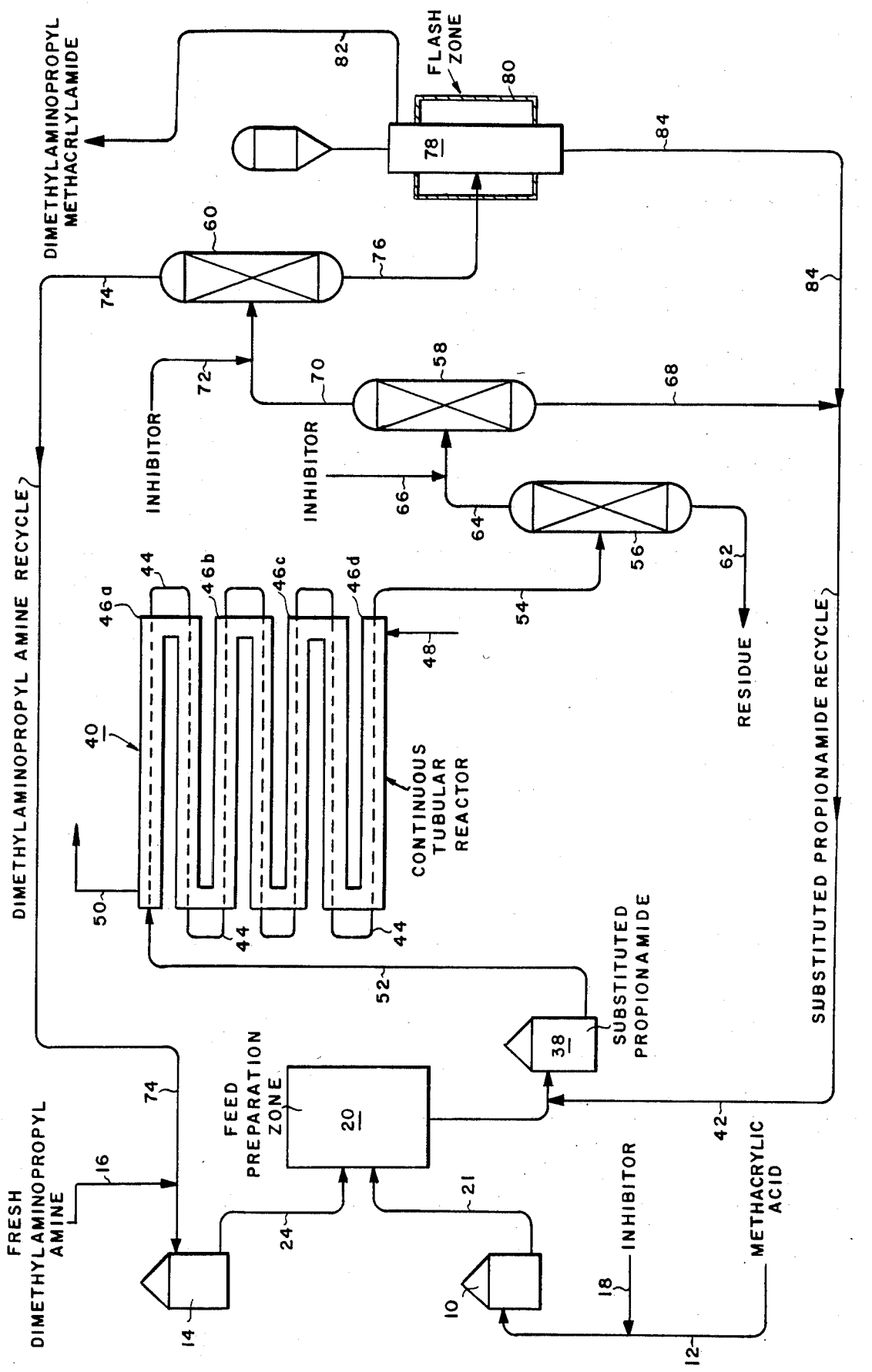

1

PROCESS FOR THE PRODUCTION OF N-(3-DIMETHYLAMINOPROPYL)METHACRYLAMIDE

BACKGROUND OF THE INVENTION

1. Field of the Invention

This invention relates to a non-catalytic method for the preparation of N-(3-dimethylaminopropyl)methacrylamide. More particularly, this invention relates to a method for the preparation of N-(3-dimethylaminopropyl)methacrylamide from N-(3-dimethylaminopropyl)-3-dimethylaminopropyl-2-methylpropionamide using a continuous tubular pyrolysis reactor.

2. Prior Art

Moss et al. U.S. Pat. No. 3,878,247 discloses a process for the production of N-(tertiary aminoalkyl) acrylamides in which an acrylic acid is first reacted with an excess of a tertiary aminoalkylamine to form a beta-aminopropionamide intermediate. In accordance with the Moss et al. invention, the propionamide intermediate is decomposed by pyrolysis at a temperature of 180° to 300° C. to the desired N-(tertiary aminoalkyl) acrylamide product and to a recyclable tertiary aminoalkylamine. By-product impurities are formed during the pyrolysis reaction and since the final product is a reactive vinyl monomer, Moss et al. teach that the product amine and the cleaved tertiary amino alkylamine should be taken overhead from the reaction mixture as formed.

U.S. Pat. No. 4,251,461 discloses an improvement in the pyrolysis reaction disclosed by Moss et al. wherein the beta-aminopropionamide is held in an atmospheric holding tank at 150° to 220° C. for 8 to 72 hours prior to pyrolysis in order to reduce the formation of by-product impurities.

SUMMARY OF THE INVENTION

Dimethylaminopropylmethacrylamide is a tertiary amine-substituted reactive monomer that can be used for the incorporation of the amino group into synthetic polymers. The polar amino group enhances adhesion and provides a specific site for dying and subsequent cross-linking. It also imparts alkaline and cationic properties to the resultant copolymer. It may also be used as a raw material for the manufacture of methacrylamidopropyltrimethylammonium chloride. Thus, N-(3-dimethylaminopropyl)methacrylamide, more commonly referred to as dimethylaminopropylmethacrylamide and frequently identified by the acronym DMAPMA, and the corresponding methacrylamidopropyltrimethylammonium chloride, sometimes referred to by the acronym MAPTAC can be used in the preparation of flocculants for clarifying water such as waste water and sewage. DMAPMA can also be used in preparation of water dispersible copolymers which can be applied to a substrate by electrodeposition. When the dimethylaminopropylacrylamide is incorporated into an acrylic fiber as a comonomer, the dyability of the resultant acrylic fiber is improved. It is also useful for the preparation of ion exchange resins and the preparation of lubricating oil additives.

Since the dimethylaminomethacrylamide monomer which is produced in accordance with the present invention is susceptible of a wide variety of uses, purity is a very important criteria insofar as utility is concerned. The removal of impurities is costly and time-consuming. Therefore, it is desirable to provide a process for the preparation of dimethylaminomethacrylamide which is characterized by minimized by-product formation.

It has been surprisingly discovered, contrary to the teaching of Moss et al., that it is not necessary to remove the dimethylaminopropylacrylamide and the recyclable dimethylaminopropyl amine as evolved during the pyrolysis reaction. To the contrary, it has been further discovered in accordance with the present invention that when the substituted propionamide feedstock for the pyrolysis reaction is subjected to pyrolysis in a closed reactor, such as a tubular reactor, under conditions to be hereinafter described in greater detail, the dimethylaminopropylmethacrylamide and dimethylaminopropylamine may be retained in the reaction mixture during the course of the pyrolysis reaction without adversely affecting the selectivity of the pyrolysis reaction. It has been further discovered, in accordance with the present invention that significantly lower levels of by-products are formed when the pyrolysis reaction is conducted under the recited pyrolysis conditions in a closed reactor system, such as a tubular reactor system.

SUMMARY OF THE PRESENT INVENTION

In accordance with the present invention the substituted propionamide raw material, N-(3-dimethylaminopropyl)-3-dimethylaminopropyl-2-methylpropionamide, is prepared by the batch reaction of N-(3-dimethylaminopropyl)amine with methacrylic acid in the molar ratio of about 2 mols of dimethylaminopropylamine per mol of methyacrylic acid. The product from the batch reaction is used as the feedstock for the pyrolysis process of the present invention wherein the substituted propionamide feedstock is continuously passed through a tubular reactor under non-catalytic pyrolysis reaction conditions including a temperature of about 180° to about 300° C., and more preferably from about 200° to about 250° C., and a residence time within the range of about 1 to 8 hours, and more preferably within the range of about 2 to 4 hours. After its passage through the continuous tubular reactor, the pyrolysis product is charged to a separation zone where the pyrolysis product is separated, as desired, into a product fraction, one or more recycle fractions and one or more discard fractions. In accordance with a preferred form of the present invention, the pyrolysis product is separated in a fractionation zone into a residue fraction which is discarded, a substituted propionamide recycle fraction which is recycled to the continuous tubular reactor, a dimethylaminopropylamine recycle fraction which is recycled to the batch reactor, and the desired product, N-(3-dimethylaminopropyl) methacrylamide, more commonly referred to as dimethylaminopropylmethacrylamide.

BRIEF DESCRIPTION OF THE DRAWINGS

In the drawings, FIG. 1 is a schematic flow sheet with conventional parts omitted showing the general reaction scheme used in the practice of the present invention.

DESCRIPTION OF THE PREFERRED EMBODIMENT

Turning now to FIG. 1, there is shown a schematic flow sheet illustrating a preferred method for practicing the process of the present invention. In the drawing conventional parts, such as valves, pumps, temperature sensors, pressure sensors, heaters, coolers, and control and flow regulation apparatus have been omitted.

The starting raw materials for the present invention are methacrylic acid which is suitably charged to a storage tank 10 by means of a feed line 12 and dimethylaminopropylamine which is suitably charged to a storage tank 14 by a charge line 16. Since methacrylic acid is a reactive vinyl monomer, it is inhibited by the addition of an appropriate polymerization inhibitor by way of line 18 such as, for example, hydroquinone, paramethoxyphenol, 2,6-di-t-butyl-para-cresol, phenothiazine, N-phenyl-2-naphthylamine, N,N-diphenyl-para-phenylenediamine, 2-mercaptobenzothiazole, powdered copper, the methyl ether of hydroquinone (MEHQ), etc. Mixtures of two or more such inhibitors may be used if desired.

As taught, for example, by Moss et al. U.S. Pat. No. 3,878,427, the substituted propionamide feedstock is prepared, in a feed preparation zone 20 utilizing conventional equipment such as an autoclave to which fresh dimethylaminopropylamine is added by way of a charge line 24 and to which methacrylic acid is added by way of a charge line 26, the reactants being charged in the molar ratio of at least about 2 mols of dimethylaminopropylamine per mol of methacrylic acid, whereby a non-catalytic condensation reaction is initiated resulting in the formation of the substituted propionamide. At the end of the reaction, the thus prepared reaction product is discharged from the feed preparation zone 20 by way of a line 36 to a storage tank 38 which constitutes the feed tank for the continuous tubular reactor 40 which is used in accordance with the present invention. Recycle substituted propionamide may also be charged to the tank 38 by way of a recycle line 42, the recycle stream being obtained in a matter to be hereinafter described.

The continuous tubular reactor of the present invention is a tubular reactor of any conventional construction such as a tubular reactor submerged in a unitary shell (not shown) or, as shown in the drawing, a continuous conduit 44 jacketed with jackets 46a, 46b, 46c, 46d, etc.; the number of jackets being consistent with the length of the tubular conduit. Heat exchange fluid may be continuously circulated through the jackets by way of a charge line 48 and a discharge line 50.

It will be understood that an amount of substituted propionamide feedstock is maintained in the stock tank 38 sufficient to permit essentially continuous flow of the substituted propionamide feedstock through the tubular reactor. To this end, a batch reactor in the feed preparation zone 20 is run as often as desired so that successive batches of the substituted propionamide feedstock may be incrementally charged to the stock tank 38 prior to its depletion.

In accordance with the preferred embodiment of the present invention a continuous tubular reactor 40 is provided having a length and diameter such that the rate of flow of the substituted propionamide feedstock therethrough will provide for a residence time within the range of 1 to 5 hours. The desired pyrolysis temperature is maintained in the tubular reactor by circulating the heat exchange fluid through the jackets surrounding the tubular reactor (e.g., "Dowtherm", a proprietary product of the Dow Chemical Company comprising a biphenyl/biphenyl oxide eutectic).

As indicated, the pyrolysis reaction that is conducted in accordance with the present invention is a non-catalytic reaction and therefore it is not necessary to provide for the use of catalyst.

To initiate the pyrolysis reaction of the present invention, the substituted propionamide feedstock is discharged from the tank 38 by way of a line 52 leading to the tubular reactor 40 at a rate such that a desired predetermined residence time is maintained, such as a residence time of 3 to 4 hours.

The entire pyrolysis product flows through the tubular reactor and no effort is made to extract the dimethylaminopropylamine or dimethylaminopropylmethacrylamide products from the tubular reactor during the course of the flow of the substituted propionamide feedstock and its pyrolysis products through the tubular reactor.

At the end of the reaction cycle, the pyrolysis reaction product is discharged from the continuous tubular reactor 40 by way of a discharge line 54 leading to a fractionation zone comprising for example, splitter columns 56, 58 and 60.

Within the first splitter column 56, the reaction product is substantially completely taken overhead as distillate, with only a residue fraction 62 being separated for discharge from the system.

The distillate from the splitter 56 is charged by way of a line 64 to a second splitter column 58 in admixture with an inhibitor solution added to line 64 by way of inhibitor charge line 66.

Within the splitter column 58, the liquid reaction product is separated into a bottoms substituted propionamide recycle fraction 58 which is charged to the recycle line 42 by way of a discharge line 68 and a distillate fraction which is charged by way of a line 70 to a third column 60. Again, one or more inhibitors is added to the overhead line 70 by way of an inhibitor charge line 72.

Within the column 60, the distillate from the column 58 is separated into a distillate dimethylaminopropylamine recycle fraction which is discharged from the column 60 by way of a line 74 leading to the dimethylaminopropylamine charge tank 14 and a bottoms fraction 76 comprising impure dimethylaminopropylmethacrylamide, which is charged to a suitable purification zone comprising, for example, a wiped film evaporator 78 provided with a jacket 80 for temperature control.

Within the wiped film evaporator 80, the crude reaction product 76 is separated into a flashed highly purified dimethylaminopropylmethacrylamide product fraction 82 which is taken overhead by way of the line 82 and a bottoms fraction comprising impure substituted propionamide which is discharged by way of a line 84 leading to the recycle line 42 for the substituted propionamide stock tank 38.

Although it is not essential to the practice of the present invention, in accordance with the preferred embodiment, the average residence time of the substituted propionamide feedstock and stock tank 38 is maintained, as disclosed in my U.S. Pat. No. 4,251,461 to provide for residence time of about 8 to about 72 hours while the substituted propionamide feedstock is maintained at a temperature of about 120° to about 240° C. and a pressure of from about 300 mm to about 1550 mm of mercury.

By way of example, about 135 parts per hour of substituted propionamide feedstock may be charged by way of the line 42 leading from the stock tank 38 to the tubular reactor 40, the charge comprising about 100 parts per hour of fresh substituted propionamide feedstock and about 35 parts per hour of recycle substituted propionamide recycled by way of the line 42.

The feedstock is suitably flowed through the pyrolysis reactor 40 at an appropriate temperature, such as a temperature within the range of about 200° to about 250° C. and a pressure of, for example, from about 50 to about 150 pounds per square inch at a flow rate suitable to provide for a residence time of about 3 to about 4 hours.

The entire pyrolysis product, including the dimethylaminopropylmethacrylamide reaction product and recycle products is discharged from the continuous tubular reactor 40 by way of the line 54 to the fractionation zone where it is separated to about 5 parts per hour of a residue fraction which is discharged from the system by way of a line 62, about 35 parts per hour of substituted propionamide recycle which is charged to the recycle line 42 by way of lines 68 and 64 and about 36 parts per hour of dimethylaminopropylamine recycle which is discharged by way of the line 74 leading to the attached, the propionamide intermediate to DMAPMA was pyrolyzed using two different reactor systems—a conventional continuous stirred tank reactor (CSTR) such as taught by Moss et al., and a lower residence time continuous tube (CT) reactor system. In Table 1, the total quantity of impurities boiling between the DMAPMA product and recyclable DMAPA in the reactor effluents are compared, using gas chromatography analysis techniques. As can be seen, the average effluent impurity level for the continuous tubular (CT) reactor was 2.2%, while the average for the overhead product from the CSTR conventional pyrolysis was 4.98%. Furthermore, the average ratio of difficult to separate impurities to recoverable DMAPMA product was 0.046 for the case of the CT reactor, and 0.086 for the conventional CSTR reactor.

Even more illustrative is that the average percent increase in impurities boiling between DMAPA and DMAPMA (over those in the feed) was 1097% in the case of the conventional CSTR reactor, and nill in the case of the CT reactor.

TABLE 1

REACTOR SYSTEM COMPARISON

| | Continuous Tube Pyrolysis Reactor | | | Continuous Stirred Tank Reactor (Conventional) | | | |
|---|---|---|---|---|---|---|---|
| | Reactor Feed | Reactor Product | Reactor Product | Reactor Feed | Reactor Product | Reactor Feed | Reactor Product |
| Area % GC: | | | | | | | |
| Lights | 0.023 | 0.154 | 0.24 | 0.040 | 0.10 | 0.021 | 0.06 |
| DMAPA | 3.35 | 22.91 | 32.88 | 3.99 | 34.61 | 16.36 | 47.22 |
| "Impurities"* | 2.75 | 2.47 | 2.71 | 3.15 | 3.46 | 0.023 | 0.97 |
| DMAPMA | 12.38 | 42.77 | 51.21 | 17.19 | 60.37 | 14.37 | 51.36 |
| Unknowns | 2.85 | 1.38 | 0.95 | 2.36 | 1.45 | 0.47 | 0.37 |
| Propionamide | 78.64 | 30.31 | 11.91 | 73.26 | ~0 | 68.73 | — |
| Ratio: Impurities*/DMAPMA | | 0.057 | 0.053 | | 0.057 | | 0.0188 |
| % Increase in Impurities over Feed | | −10.3 | −2 | | +10 | | +4136 |
| Reactor temperature, °C. | | 235 | 250 | | 260 | | 236 |
| Run No. | | 4907-60-19 | 4907-60-38 | | F7-537-1 | | F7-623-23 |
| Area % GC: | | | | | | | |
| Lights | 0.072 | 0.181 | 0.27 | 0.0912 | 0.08 | 0.086 | 0.05 |
| DMAPA | 2.98 | 23.46 | 29.88 | 10.36 | 32.39 | 17.58 | 34.06 |
| "Impurities"* | 1.79 | 1.87 | 1.86 | 2.89 | 9.6 | 5.26 | 5.91 |
| DMAPMA | 19.44 | 46.3 | 53.68 | 15.04 | 56.72 | 14.83 | 59.05 |
| Unknowns | 1.72 | 1.34 | 1.47 | 2.10 | 0.90 | 1.54 | 0.54 |
| Propionamide | 73.21 | 26.26 | 12.28 | 68.83 | 0.29 | 60.19 | 0.37 |
| Ratio: Impurities*/DMAPMA | | 0.04 | 0.035 | | 0.1693 | | 0.10 |
| % Increase in impurities* over Feed | | +4.4 | +4.0 | | +232 | | +12.2 |
| Reactor temperature, °C. | | 235 | 250 | | 252 | | ~242 |
| Run No. | | 4907-61-14 | 4907-61-24 | | F7-558-24 | | F7-565-23 |
| Avg. ratio Impurities*/DMAPMA | | | 0.046 | | | 0.086 | |
| Avg. % Increase in impurities* over Feed | | | −1% | | | 1097 | |
| Avg. impurity* level in Reactor Product | | | 2.2 | | | 4.98 | |

*Notes
"Impurities" refers only to those impurities appearing between DMAPA and DMAPMA on the GLC tracer.

feed tank 14. About 59 parts per hour of purified dimethylaminopropylmethacrylamide is recovered by way of the line 82.

It will be understood that the relative ratios of the streams will vary, depending on the particular correlation of reaction conditions employed and the particular separation sequence that is used.

.EXAMPLES

In order to demonstrate the improvement obtained with the process of the present invention as compared to a pyrolysis reaction as taught by Moss et al. wherein the desired product and the cleaved tertiary amino alkylamine are removed, as evolved, several low residence time reactor schemes were utilized. In Table 1, As will be seen from the foregoing table, the reaction product prepared by the continuous pyrolysis reaction of the present invention is characterized by significant reduction in impurities in contrasted with the conventional pyrolysis method of Moss et al. U.S. Pat. No. 3,878,347. It will also be noted that the improvement in impurity levels was more pronounced at the lower reaction temperature of 235° C. than at the higher reaction temperature, but nevertheless was significantly lower than that experienced in a conventional pyrolysis reaction.

It will be understood that the foregoing examples have been given by way of illustration only and are not intended as limitations on the scope of this invention, which is defined solely by the appended claims.

What is claimed is:

1. In a method wherein N-(3-dimethylaminopropyl)-3-dimethylaminopropyl-2-methylpropionamide is pyrolyzed to provide a reaction product comprising a dimethylaminopropylmethacrylamide (DMAPMA) product, a dimethylaminopropylamine (DMAPA) recycle and a N-(3-dimethylaminopropyl)-3-dimethylaminopropyl-2-methylpropionamide recycle, the improvement for obtaining a reaction product containing a reduced percentage of impurities boiling between DMAPA and DMAPMA which comprises conducting said pyrolysis reaction in a continuous tubular reactor at a temperature within the range of about 180° to about 300° C., a pressure of about 50 to about 150 psig., an average residence time from about 1 to about 6 hours and thereafter separating the continuous tubular reactor product containing a reduced percentage of said impurities in a fractionation zone into a purified dimethylaminopropylmethacrylamide product fraction, a dimethylaminopropylamine recycle fraction and a substituted propionamide recycle fraction.

2. A method as in claim 1 wherein the pyrolysis conditions include a residence time of about 2 to about 4 hours and a temperature within the range of about 200° to about 250° C.

3. A method for the preparation of dimethylaminopropylmethylacrylamide (DMAPMA) which comprises reacting dimethylaminopropylamine (DMAPA) with methacrylic acid in a first batch reaction zone in the molar ratio of about 2 moles of dimethylaminopropylamine per mol of methacrylic acid to provide a first reaction product comprising N-(3-dimethylaminopropyl)-3-dimethylaminopropyl-2-methylpropionamide, charging said first N-(3-dimethylaminopropyl)-3-dimethylaminopropyl-2-methylpropionamide reaction product to a second continuous tubular pyrolysis zone and subjecting the same therein to pyrolysis conditions incluidng a temperature within the range of about 180° to about 300° C. and a residence time within the range of about 1 to about 6 hours to provide a second pyrolysis reaction product having a reduced percentage of impurities boiling between DMAPA and DMAPMA as compared with said first reaction product, and thereafter fractionating said second pyrolysis product into a dimethylaminopropylmethylacrylamide product fraction, a dimethylaminopropylamine recycle fraction which is recycled to said first batch reactor and an impure N-(3-dimethylaminopropyl)-3-dimethylpropyl-2-methylpropionamide recycle fraction which is recycled to said second continuous tubular pyrolysis reaction zone.

4. A method as in claim 3 wherein the pyrolysis reaction conditions include a temperature within the range of about 200° to about 250° C. and a residence time within the range of about 1 to about 6 hours.

* * * * *